United States Patent [19]

Cox

[11] Patent Number: 4,485,238
[45] Date of Patent: Nov. 27, 1984

[54] PREPARATION OF (((6-SUBSTITUTED PHENOXY-2-PYRIDINYL)-METHYL)-3-(2,2-BIS(TRIFLUOROMETHYL)-1-ETHENYL)-2,2-DIMETHYLCYCLOPROPANE CARBOXYLATES

[75] Inventor: Donald L. Cox, Concord, Calif.

[73] Assignee: The Dow Chemical Company, Midland, Mich.

[21] Appl. No.: 511,411

[22] Filed: Jul. 6, 1983

Related U.S. Application Data

[63] Continuation of Ser. No. 331,411, Dec. 16, 1981, abandoned.

[51] Int. Cl.$^3$ .................. C07D 213/64; C07D 491/04
[52] U.S. Cl. .................... 546/300; 546/270; 424/263
[58] Field of Search ................ 546/270, 300

[56] References Cited

U.S. PATENT DOCUMENTS

| | | |
|---|---|---|
| 3,961,070 | 6/1976 | Davis et al. ......................... 424/304 |
| 3,962,458 | 6/1976 | Schrider ............................. 424/304 |
| 3,979,519 | 9/1976 | Punja .................................. 424/304 |
| 3,987,079 | 10/1976 | Kay et al. ......................... 260/465 F |
| 4,000,181 | 12/1976 | Elliott et al. ...................... 424/304 |
| 4,163,787 | 8/1979 | Malhotra et al. ................... 424/263 |
| 4,221,799 | 9/1980 | Van Heertum et al. ............ 424/263 |
| 4,228,172 | 10/1980 | Malhotra et al. ................... 424/263 |
| 4,256,893 | 3/1981 | Malhotra et al. ................... 546/301 |
| 4,262,001 | 4/1981 | Malhotra et al. ................... 424/263 |
| 4,342,770 | 8/1982 | Clifford et al. ..................... 424/263 |

FOREIGN PATENT DOCUMENTS

| | | |
|---|---|---|
| 2547534 | 4/1976 | Fed. Rep. of Germany ... 260/465 D |
| 6011106 | 4/1976 | Japan .................................. 560/73 |
| 0753211 | 5/1975 | South Africa ..................... 424/314 |

*Primary Examiner*—Alan L. Rotman
*Attorney, Agent, or Firm*—S. Preston Jones; Ronald G. Brookens

[57] ABSTRACT

((6-(Substituted phenoxy)-2-pyridinyl)methyl)-3-(2,2-bis(trifluoromethyl)-1-ethenyl)-2,2-dimethylcyclopropane carboxylates and the geometric and optical isomers thereof are prepared by the reaction of an appropriate cyano((6-(substituted phenoxy)-2-pyridinyl)methyl)-2,2-dimethyl-3-cyclopropane carboxaldehyde with tetrakis(trifluoromethyl)-1,3-dithioetane. These compounds exhibit a high degree of insecticidal activity and are so employed.

2 Claims, No Drawings

PREPARATION OF ((6-SUBSTITUTED PHENOXY-2-PYRIDINYL)-METHYL)-3-(2,2-BIS(-TRIFLUOROMETHYL)-1-ETHENYL)-2,2-DIMETHYLCYCLOPROPANE CARBOXYLATES

CROSS-REFERENCE TO RELATED APPLICATION

This is a continuation of application Ser. No. 331,411, filed Dec. 16, 1981 now abandoned.

DESCRIPTION OF PRIOR ART

Various insecticidal compounds which are esters of cyclopropane carboxylic acid are known. 3-(Fluorophenoxy)benzyl substituted cyclopropane carboxylates are taught in German Pat. No. 2,547,534. 3-Phenoxybenzyl cyclopropane carboxylates are also taught in Japanese Pat. No. 6,011,106. Phenoxy phenyl substituted cyclopropane carboxylates are taught as insecticides and acaricides in U.S. Pat. No. 3,961,070 and as tick control agents in South African Pat. No. 7,503,211 (based on U.S. patent application Ser. No. 487,417 filed Oct. 7, 1974). Other related substituted phenyl esters of cyclopropane carboxylic acids are taught in French Pat. No. 2,281,918. Various insecticidal 3-(dihalovinyloxy)-benzyl esters of cyclopropane carboxylic acid are taught in German Pat. No. 2,554,883 and ectoparasites are taught to be controlled by the use of 3-phenoxybenzyl esters of spirocarboxylic acids in U.S. Pat. No. 3,962,458. In addition, U.S. Pat. No. 3,979,519 teaches 3-(2,2-dihalovinyloxy)benzyl-2-(2,2-dihalovinyl)-3,3-dialkylcyclopropane carboxylates as insecticides. Additionally, phenoxy pyridine methyl esters of cyclopropane carboxylic acids are taught in U.S. Pat. No. 4,163,787.

SUMMARY OF THE INVENTION

The present invention is directed to the preparation of ((6-(substituted phenoxy)-2-pyridinyl)methyl)-3-(2,2-bis(trifluoromethyl)-1-ethenyl)-2,2-dimethylcyclopropane carboxylates compounds corresponding to the formula

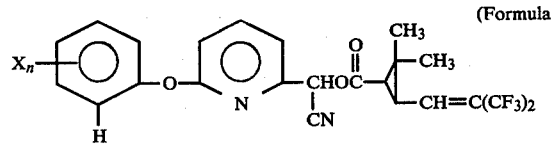

(Formula I)

wherein X independently represents hydrogen, alkyl of 1 to 4 carbon atoms, alkoxy of 1 to 4 carbon atoms, alkylthio of 1 to 4 carbon atoms, alkylsulfonyl of 1 to 4 carbon atoms, trifluoromethyl, 3,4-methylenedioxy, chloro, fluoro or bromo; R represents hydrogen, cyano or ethenyl and n represents an integer of 1 or 2. These compounds are employed as intermediates in the preparation of compounds which have a high degree of insecticidal activity.

The compounds produced by the process the present invention contain the optically active centers

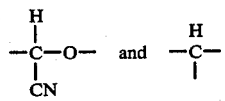

and can exist in several geometric isomeric forms such as cis- or trans-configurations, as well as in several optically active stereoisomeric forms such as the dextrorotatory and levorotatory forms of each of the above configurations. The various mixtures and racemates of the above isomers are within the scope of the present invention. Additionally, the dextrorotatory forms of such compounds have been found to be more active biologically than the levorotatory form and may be resolved and used whenever the greater activity justifies the extra expenses of isolating the more active isomer.

A general discussion of the isomer activity difference phenomenon can be found in A. Albert, *Selective Toxicity*, 4th Ed. Met Luen & Co., Ltd., London, 1968, pp. 387–390 and more particular discussions in A. Fredga and B. Åberg, "Stereoisomerism in plant growth regulators of the auxin type:, *Ann. Rev. Plant Physiology* 16:53–72, 1965 and in E. J. Lien, J. F. R. DeMiranda and E. J. Airens, "Quantitative structure-activity correlation of optical isomers", *Molecular Pharmacology* 12:598–604, 1976.

The compounds produced by the process of the present invention are high boiling materials having low mammalian toxicity. The compounds are substantially insoluble in water and moderately soluble in common organic solvents.

The compounds can be prepared by a method which comprises reacting, under anhydrous conditions, from about 1 to about 2 moles of an appropriate ((6-(substituted phenoxy)-2-pyridinyl)methyl)-2,2-dimethyl-3-cyclopropanecarboxaldehyde with about one mole of tetrakis(trifluoromethyl)-1,3-dithioetane in the presence of a solvent such as for example ethyl ether, methylene chloride, or toluene and from about 1 to about 4 moles of triphenyl phosphine temperature of from about minus (−) 100° C. to about minus (−) 20° C. and at ambient pressures for from about one to about 24 hours. The reaction scheme is as follows:

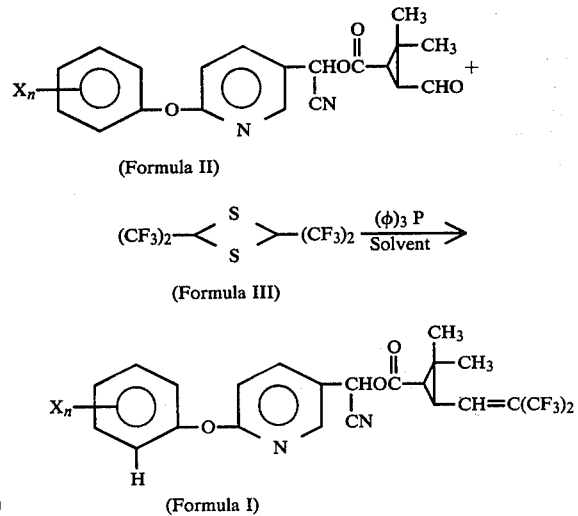

wherein X and n are as hereinabove defined.

The above is not being presented as a balanced equation.

At the completion of the reaction, the reaction mixture is allowed to return to room temperature and it is then extracted with a solvent such as for example hexane, ethyl ether, methylene chloride or toluene. The extract is filtered to remove insolubles and the crude product separated by conventional separatory techniques such as for example distillation, solvent removal by evaporation and the like. The product can be further purified if desired by solvent extraction or liquid phase chromatographic techniques.

In accordance with the present invention, it should be understood that the various geometric isomers as well as the mixed compound can be prepared by the procedures taught herein.

DESCRIPTION OF SOME PREFERRED EMBODIMENTS

The following examples illustrate the present invention and the manner by which it can be practiced but, as such, should not be construed as limitations upon the overall scope of the same.

EXAMPLE I

Cyano((6-phenoxy-2-pyridinyl)methyl)-3-(2,2-bis(trifluoromethyl)-1-ethenyl)-2,2-dimethyl cyclopropane carboxylate

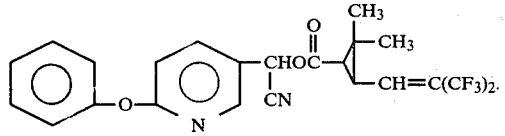

To a 100 ml round bottom flask, under an argon atmosphere was added 3.0 g (8.5 millimoles (mmol)) of cyano((6-phenoxy-2-pyridinyl)methyl)-2,2-dimethyl-3-cyclopropanecarboxaldehyde, 4.6 g (17.4 mmol) of triphenylphosphine and 50 ml of diethyl ether. The temperature of the stirring mixture was reduced to −75° C. To this mixture was added 2.0 g (5.5 mmol) of tetrakis-(trifluoromethyl)-1,3-dithioetane. Stirring was continued for 4 hours at the above temperature. The mixture was then allowed to slowly reach room temperature over a period of about 20 hours. The mixture was extracted with hexane and the extract filtered through silica gel to remove any triphenylphosphine contained therein. The crude product was separated from the extract by distillation. The product was then purified by preparative high pressure liquid chromatography and recovered in a yield of 1.3 g (32 percent of theory) as an oil. The cyano((6-phenoxy-2-pyridinyl)methyl)-3-(2,2-bis(trifluoromethyl)-1-ethenyl)-2,2-dimethylcyclopropane carboxylate product thus prepared had a refractive index of N(26.3/D)=1.5019. Upon analysis, the compond was found to have carbon, hydrogen and nitrogen contents of 57.12, 3.91 and 5.61 percent, respectively, as compared with the theoretical contents of 57.02, 3.75 and 5.78 percent, respectively, as calculated for the above named compound. The structure of the compound was confirmed by its nuclear magnetic resonance (NMR) and its infrared spectrum (IR).

EXAMPLE II

Tetrakis(trifluoromethyl)-1,3-dithioetane

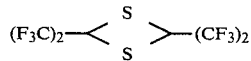

To a 2 liter stainless steel reactor bomb was added, at room temperature, 100 g (0.67 mole) of perfluoropropene, 21.5 g (0.67 mole) of sulfur, 2.3 g (40 mmol) of potassium fluoride and 300 ml of sulfolane. The bomb was sealed and the temperature raised to 120° C. and held there for 12 hours. At the completion of the reaction time, a dark brown heterogenous mixture was obtained. The mixture was distilled and the 110°–115° C. fraction was recovered. The tetrakis(trifluoromethyl)-1,3-dithioetane product was recovered as a faintly blue-green clear liquid in a yield of 29 g. The NMR and IR spectrums confirmed the structure of the product. Upon analysis, the product was found to have carbon, fluorine and sulfur contents of 19.44, 62.58 and 17.18 percent, respectively, as compared with the theoretical contents of 19.79, 62.62 and 17.61 percent, respectively, as calculated for the above named compound.

The ((6-(substituted phenoxy)-2-pyridinyl)methyl-2,2-dimethylcyclopropane carboxaldehydes corresponding to the formula

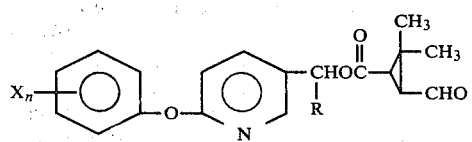

and which are employed as starting materials can be prepared by the reaction, at room temperature, of substantially equal moles of an appropriate (6-phenoxy-2-pyridinyl)methanol with 3-formyl-2,2-dimethylcyclopropane carboxylic acid in the presence of a solvent such as pyridine, dichlorotoluene, toluene or methylene chloride. Additionally, the reaction is conducted in the presence of p-toluene sulfonic acid and dicyclohexyl carbodiimide.

The reaction is usually complete in from about 12 to about 48 hours and the crude product thus obtained can be purified by filtering to remove insolubles and removing the solvent therefrom.

The product is usually further purified by extracting the product from the resulting residue with a solvent such as diethyl ether and the ether extract is washed with weak hydrochloric acid followed by washing with water. The extract is dried and the solvent is removed. The desired product is then recovered by distillation.

EXAMPLE III

Cyano((6-phenoxy-2-pyridinyl)methyl)-2,2-dimethyl-3-cyclopropanecarboxaldehyde

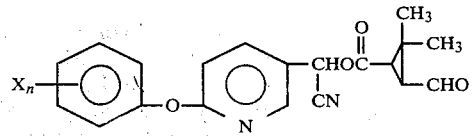

To a 250 ml round bottom flask was added 6.0 g (26.7 mmol) of cyano(6-phenoxy-2-pyridinyl)methanol, 3.8 g (26.7 mmol) of 3-formyl-2,2-dimethylcyclopropane carboxylic acid and 60 ml of pyridine. The mixture was stirred to assure homogeneity and 0.28 g (1.45 mmol) of p-toluene sulfonic acid was added. Stirring was maintained for 15 minutes and then 6.30 g (30.4 mmol) of dicyclohexyl carbodiimide, dissolved in a minimum amount of pyridine, was added. The reaction mixture was stirred at room temperature for 24 hours. At the completion of this time, the reaction mixture was filtered and then the solvent was removed by evaporation under reduced pressure. The residue was taken up in diethyl ether and extracted three times with equal volumes of 2 normal hydrochloric acid and water, respectively. The mixture was dried over magnesium sulfate, filtered and the solvent removed by evaporation under reduced pressure. The desired cyano((6-phenoxy-2-pyridinyl)methyl)-2,2-dimethyl-3-cyclopropane carboxaldehyde product was recovered by distillation at 140° C. and 0.1 torr in a yield of 3.0 grams.

EXAMPLE IV

3-Formyl-2,2-dimethylcyclopropane carboxylic acid

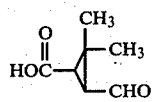

To a 250 ml round bottom flask was added 10.0 g (58.8 mmol) of ethyl 3-formyl-2,2-dimethylcyclopropane carboxylate, 2.8 g (70.6 mmol) of sodium hydroxide (added as 5.6 g of 50 percent sodium hydroxide) and 150 ml of methanol. The mixture was stirred and brought to reflux over a 115° C. oil bath. After a 20 minute reaction period, the mixture was concentrated to a 25 percent solvent volume by evaporation under reduced pressure. The mixture was brought back to the original volume by the addition of 2N hydrochloric acid. The mixture was extracted with ethyl acetate and the extract dried over magnesium sulfate, filtered and concentrated by evaporation under reduced pressure. An NMR of the material indicated that hydrolysis was not complete. Therefore, a 1.5 molar equivalent of potassium hydroxide and 150 ml of methanol were added. The stirred mixture was then refluxed for three hours. The reaction mixture was worked-up as above and a yellow-moderately viscous oil was obtained. The NMR and IR spectra's confirmed the products.

The ethyl 3-formyl-2,2-dimethylcyclopropane carboxylate employed as a starting material is a well known compound.

In accordance with the present invention, it has been found that the ((6-(substituted phenoxy)-2-pyridinyl)-methyl)-3-(2,2-bis(trifluoromethyl)ethenyl)-2,2-dimethylcyclopropane carboxylates possess insecticidal properties. The compounds have quick knockdown activity and low persistence, as toxic residues, and has low mammalian toxicity.

Because of the "quick knockdown", the active compounds are particularly suitable for the control, inside houses, barns, warehouses, public buildings, and the like, of pests, including cockroaches, such as the German cockroach, American cockroach, and brown-banded cockroach; beetles, such as the black-carpet beetle, confused flour beetle, saw-tooth grain beetle and larder beetle; spiders, silverfish, bedbugs; fleas, such as those on bedding used by household pets, and flea larvae; mosquitos; boxelder bugs; spiders; mites; ants; centipedes; and flies, such as hornfly, stable fly and facefly and the common housefly. The active compounds are highly effective for such indoor control of insect pests and thus are particularly adapted for such employment. In addition, the active compounds are also useful for the control of lice and ticks and other insects parasitic to animals.

The compounds of the present invention are very effective for the control of the many insect pests found on the roots or aerial portions of growing plants, including aphids, scale, mites, and chewing and sucking insects, such as leafhopper, Southern army worm, two-spotted spider mite, cotton aphid, cabbage looper, western spotted cucumber beetle, boolworm, codling moth, beet armyworm, and tobacco budworm.

When applied to plants, plant parts, and their habitats the active compounds protect the plants from the attack of insect pests, exhibit residual control of the insects over only a relatively short period of time thereby not having appreciable build-up in the environment.

In some procedures, the compounds can be vaporized or sprayed or distributed as aerosols into the air, or onto surfaces in contact with the air. In such applications, the compounds manifest the useful properties hereinbefore described.

The methods of the present invention comprise contacting an insect with an insecticidally effective or inactivating amount of one or more of the compounds of the present invention.

The contacting can be effected by application of one or more of the compound to the habitat of the insects. Representative habitats include soil, air, water, food, vegetation, inert objects, stored matter such as grains, other animal organisms, and the like. The inactivation can be lethal, immediately, or with delay, or can be a sub-lethal one in which the inactivated insect is not able to carry out one or more of its normal life processes. This latter situation prevails when one of the systems of the insect, typically the nervous system, is seriously disturbed. A preferred embodiment of the present invention comprises the employment of the present method for the kill and control of insects; such employment gives excellent results, particularly in control of insects that have developed resistance against other pest-control substances.

The inactivation of an insect by the application of an insecticidally effective or inactivating amount of an active compound of the present invention is critical to the method of the present invention. The active compound can sometimes be employed in unmodified form. Frequently, however, for easier application, the compound is modified by the employment with it of a pesticidal adjuvant or inert carrier therefor. Thus, for example, the present compounds have low solubility in water but are relatively soluble in oils, including plant essential oils. Therefore, the practical enjoyment of the beneficial utilities of the present compound often requires that the compound be composited with one or more pesticidal adjuvant substances, and the resulting compositions are comprehended within the present invention.

The compositions can be formulated in various forms, such as emulsifiable concentrates, wettable powders, flowable suspension dusts, granules, microencapsulated granules, fine granules, oil sprays, aerosols, heating fumigants (e.g. mosquito coils, electric mosquito killer mat, etc.), fogging mists, non-heating fumigants and poisonous baits and the adjuvant employed can be any one or a plurality of materials including aromatic solvents, petroleum distillates, water, or other liquid carriers, propellant substances, surface-active dispersing agents, light absorbers, and finely divided carrier solids. In such compositions, the adjuvant cooperates with the active compound so as to obtain a composition to facilitate the method of the present invention, and to obtain an improved result. The use of either a surface-active dispersing agent or a finely divided carrier solid and the use of both a surface-active dispersing agent and a finely divided carrier solid, simultaneously, constitute period embodiments of the method of the present invention. Another preferred embodiment of the present invention is a composition comprising one or more of the presently claimed compounds, an organic liquid as a solvent and carrier therefor, and a propellant material. Numerous other embodiments will become available to those skilled in the art in view of the teachings set forth hereinbelow.

The exact concentration of the active compound in a composition thereof with an adjuvant therefor can vary; it is only necessary that the active compounds be present in a sufficient amount so as to make possible the application of an insecticidally effective or inactivating dosage. Generally, for practical applications, the active compounds can be broadly applied to insect pest organisms or their habitat in compositions containing from about 0.00001 percent to about 98 percent by weight of the active compound.

In preparation of dust compositions, the product can be compounded with any of the finely divided carrier solids such as prophyllite, diatomaceous earth, gypsum and the like. In such operations, the finely divided carrier is ground or mixed with the active compound, as active agent, or wetted with a solution of the active agent in a volatile organic solvent. Similarly, dust compositions containing the active product can be similarly compounded from various of the solid dispersing agents, such as fuller's earth, attapulgite and other clays. These dust compositions can be employed as treating compositions or can be employed as concentrates and subsequently diluted with additional solid dispersing agent or with pyrophyllite, diatomaceous earth, gypsum and the like to obtain the desired amount of active agent in a treating composition. Also, such dust compositions can be dispersed in water, with or without the aid or surfactant, to form spray mixtures.

Further, the active compound or a dust concentrate composition containing said compound can be incorporated in intimate mixture with surface active dispersing agents such as ionic and nonionic emulsifying agents to form spray concentrates. Such concentrates are readily dispersible in liquid carriers to form sprays containing the toxicant in any desired amount. The choice of dispersing agent and amount thereof employed are determined by the ability of the agent to facilitate the dispersion of the concentrate in the liquid carrier to produce the desired spray composition.

In the preparation of liquid compositions, the active compound can be compounded with a suitable water-immiscible organic liquid and surface-active dispersing agent to produce an emulsifiable liquid concentrate which can be further diluted with water and oil to form spray mixtures in the form of oil-in-water emulsions. In such compositions, the carrier comprises an aqueous emulsion, that is, a mixture of water-immiscible solvent, emulsifying agent and water. Preferred dispersing agents to be employed in these compositions are oil-soluble and include the nonionic emulsifiers such as the polyoxyethylene derivatives of sorbitan esters, complex ether alcohols and the like. However, oil-soluble ionic emulsifying agents such as mahogany soaps can also be used. Suitable organic liquids to be employed in the compositions include petroleum oils and distillates, toluene liquid halohydrocarbons and synthetic organic oils.

When operating in accordance with the present invention, the active compound or a composition containing the active compound is applied to the insects to be controlled directly, or by means of application to a portion or portions of their habitat in any convenient manner, for example, by means of hand dusters or sprayers or by simple mixing with the food to be ingested by the organisms. Application to the foliage of plants is conveniently carried out with power dusters, boom sprayers and fog sprayers. In such foliar applications, the employed compositions should not contain any appreciable amounts of any phytotoxic diluents. In large scale operations, dusts, or low-volume sprays can be applied from an airplane.

In further embodiments, one of the compounds of the present invention or compositions containing the same, can be advantageously employed in combination with one or more additional pesticidal compounds. Such additional pesticidal compounds may be insecticides, nematocides, arthropodicides, herbicides, fungicides or bactericides that are compatible with the compounds of the present invention in the medium selected for application and not antagonistic to the activity of the present compounds. Accordingly, in such embodiments, the pesticidal compound is employed as a supplemental toxicant for the same or for a different pesticidal use, or as an additament. The compounds in combination can generally be present in the ratio of from 1 to 100 parts of the compound of the present invention with from 100 to 1 parts of the additional compound(s).

A preferred and especially convenient matter for the application of one or more of the present products comprises the use of a self-pressurized back formulation which can be used, for example, as a space or surface spray. Such a formulation can comprise the compound, an organic liquid as a solvent and vehicle therefor, and a propellant material which can be a condensed and compressed gas or a substance which, at room temperature, is a gas under atmospheric pressure but which liquifies under superatmospheric pressure. Where the propellant material is of the latter type, the self-pressurized pack formulation is often spoken of as an aerosol. Representative propellants include propane, butane, nitrogen, and the fluorinated hydrocarbons, such as dichlorodifluoromethane and trichlorofluoromethane. Generally, the propellant constitutes from 25 to 95 percent by weight of the total self-pressurized pack. As vehicle, there can be employed any liquid in which the desired amount of product is capable of being dispersed; preferred vehicles include petroleum distillates, kerosene, and methylene chloride. The self-pressurized pack formulation can also include other materials, such as other biologically active agents or synergists. For further discussion of the use of self-pressurized pack formulation, see U.S. Pat. Nos. 1,892,750 and 2,321,023.

EXAMPLE V

In this operation, an aqueous dispersion was prepared by admixing cyano((6-phenoxy-2-pyridinyl)methyl)-3-(2,2-bis(trifluoromethyl)-1-ethenyl)-2,2-dimethyl cyclopropane carboxylate with a predetermined quantity of water and a predetermined amount of a surfactant to give aqueous dispersions containing varying predetermined amounts of one of the compounds as the sole active toxicant. Separate cotton plant leaves were thoroughly wetted briefly with one of the dispersions and the wetted leaves placed in an open petri dish and permitted to dry. After the leaves were dried, 5 live beet armyworm larvae were placed in each petri dish. In identical operations, 5 live beet armyworm larvae were placed in control petri dishes, the leaf therein having been wetted with a solution containing only water and surfactant. The dishes were maintained under moist conditions conductive for the growth of the beet armyworm larvae for a period of about 5 days. At the end of the 5-day period, the dishes were examined and it was found that at a concentration of 400 ppm, cyano((6-phenoxy-2-pyridinyl)methyl)-3-(2,2-bis(trifluoromethyl)-1-ethenyl)-2,2-dimethyl cyclopropane carboxylate gave 100 percent kill and control of beet armyworm larvae.

EXAMPLE VI

In this operation, an aqueous dispersion was prepared by admixing cyano((6-phenoxy-2-pyridinyl)methyl)-3-(2,2-bis(trifluoromethyl)-1-ethenyl)-2,2-dimethyl cyclopropane carboxylate with a predetermined quantity of water and a predetermined amount of a surfactant to give aqueous dispersions of varying predetermined amounts of the compound as the sole active toxicant. Separate 3 inch discs cut from tobacco plant leaves were thoroughly wetted briefly with one of the dispersions and the wetted leaves placed in an open petri dish and permitted to dry. After the leaves were dried, 5 live tobacco budworm larvae were placed in each petri dish. In identical operations, 5 live tobacco budworm larvae were placed in control petri dishes, the leaf therein having been wetted with a solution containing only water and surfactant. The dishes were maintained under moist conditions conducive for the growth of the tobacco budworm larvae for a period of about 2 days. At the end of the 2-day period, the dishes were examined and it was found that at a concentration of 100 ppm, cyano((6-phenoxy-2-pyridinyl)methyl)-3-(2,2-bis(trifluoromethyl)-1-ethenyl)-2,2-dimethyl cyclopropane carboxylate gave 100 percent kill and control of tobacco budworm larvae.

EXAMPLE VII

Aqueous dispersions were prepared by admixing cyano((6-phenoxy-2-pyridinyl)methyl)-3-(2,2-bis(trifluoromethyl)-1-ethenyl)-2,2-dimethyl cyclopropane carboxylate with a predetermined quantity of water and a predetermined amount of a surfactant to give aqueous dispersions containing varying predetermined amounts of the compound as the sole toxicant. Separate rice plants were dipped into one of the dispersions and permitted to dry. A plastic cylinder was placed around the plants and 10 adult Aster leafhoppers were placed in the cylinder and the cylinder capped. In a like manner, 10 adult Aster leafhoppers were placed on control plants which had been dipped in a solution containing only water and surfactant. The plants were maintained under conditions conducive to the growth of the plants and leafhoppers. After a period of two days, the cylinder and plants were examined and it was found that at a concentration of 25 ppm, the hereinabove set forth active compound gave 100 percent kill and control of Aster leafhoppers.

EXAMPLE VIII

Aqueous dispersions were prepared by admixing a predetermined amount of cyano((6-phenoxy-2-pyridinyl)methyl)-3-(2,2-bis(trifluoromethyl)-1-ethenyl)-2,2-dimethylcyclopropane carboxylate dissolved in acetone with a predetermined quantity of water and a predetermined amount of a surfactant to give aqueous dispersions containing varying predetermined amounts of the compound as the sole toxicant. Separate cotton plants were infested with approximately 100 two-spotted spider mites and the plants dipped into one of the dispersions. In a like manner, approximately 100 two-spotted spider mites were placed on control plants and the plants sprayed to run off with a solution containing only water and surfactant. The plants were maintained under conditions conducive to the growth of the plants and mites. After a period of five days, the plants were examined to determine the minimum concentration in parts of the active compound per million parts of the ultimate dispersion necessary to give at least 95 percent kill and control of the two-spotted spider mites.

This examination determined the minimum concentration in parts of the active compound per million parts of the ultimate dispersion to about 25 ppm.

What is claimed is:

1. A method for preparing a compound corresponding to the formula

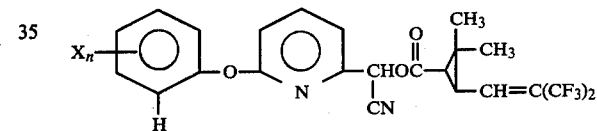

wherein X independently represents hydrogen, alkyl of 1 to 4 carbon atoms, alkoxy of 1 to 4 carbon atoms, alkylthio of 1 to 4 carbon atoms, alkylsulfonyl of 1 to 4 carbon atoms, trifluoromethyl, 3,4-methylenedioxy, chloro, fluoro or bromo and n represents an integer of 1 or 2 which comprises reacting, under anhydrous conditions and at a temperature of from about minus 100° to about minus 20° C., from about 1 to about 2 moles of an appropriate cyano ((6-(substituted phenoxy)-2-pyridinyl)methyl)-2,2-dimethyl-3-cyclopropanecarboxyaldehyde with about one mole of tetrakis (trifluoromethyl)-1,3-dithioetane in the presence of triphenyl phosphine and a solvent.

2. The method of claim 1 wherein the compound prepared is cyano((6-phenoxy-2-pyridinyl)methyl)-3-(2,2-bis(trifluoromethyl)-1-ethenyl)-2,2-dimethylcyclopropane carboxylate.

* * * * *